United States Patent
Loepfe et al.

[11] Patent Number: 5,874,314
[45] Date of Patent: Feb. 23, 1999

[54] METHOD FOR DETECTING ORGANIC VAPORS AND AEROSOLS

[75] Inventors: Markus Loepfe; Dieter Wieser, both of Zürich; Peter Ryser, Stäfa, all of Switzerland

[73] Assignee: Cerberus AG, Maennedorf, Switzerland

[21] Appl. No.: 791,623

[22] Filed: Jan. 31, 1997

[30] Foreign Application Priority Data

Feb. 3, 1996 [EP] European Pat. Off. .............. 96101563

[51] Int. Cl.⁶ .................................................. G01N 27/62
[52] U.S. Cl. ........................... 436/111; 436/106; 436/110; 436/153; 422/90; 422/98; 250/423 R; 250/424; 250/425
[58] Field of Search ...................... 436/111, 106, 436/143, 144, 149, 153, 157; 422/90, 88, 94, 98; 250/423 R, 424, 425

[56] References Cited

U.S. PATENT DOCUMENTS

| | | | |
|---|---|---|---|
| 3,808,433 | 4/1974 | Fite et al. | 250/251 |
| 4,162,404 | 7/1979 | Fite et al. | 250/423 R |
| 4,176,311 | 11/1979 | Davis | 324/468 |
| 4,209,693 | 6/1980 | Fite et al. | 250/251 |
| 4,980,557 | 12/1990 | Myers et al. | 250/423 R |
| 5,014,009 | 5/1991 | Arimoto et al. | 324/468 |
| 5,028,544 | 7/1991 | Rasulev et al. | 436/161 |
| 5,426,056 | 6/1995 | Nacson | 436/91 |

FOREIGN PATENT DOCUMENTS

| | | |
|---|---|---|
| 0262223 | 4/1988 | European Pat. Off. . |
| 0375788 | 7/1990 | European Pat. Off. . |
| 2587122 | 3/1987 | France . |
| 2281627 | 3/1995 | United Kingdom . |

OTHER PUBLICATIONS

U. Kh. Rasulev et al., "Chromatography Determination of Trace Amounts of Amines Using a Surface Ionization Detector", Journal of Chromatography A, vol. 704, No. 2 (Jun. 9, 1995), pp. 473–482.

Primary Examiner—Long V. Le
Attorney, Agent, or Firm—Baker & Botts, L.L.P.

[57] ABSTRACT

In a technique for detecting organic vapors and aerosols, e.g. of amines, hydrazines and nitrogen-containing compounds produced in combustion, molecules condense at a surface of a conductive device. By heating the conductive device in pulsed fashion, e.g. by resistance heating, condensed molecules are thermally ionized and emitted from the conductive device. Emitted ions are collected by a collector electrode, and the resulting ionic current pulse is amplified by a transimpedance circuit. The heat pulse lasts until the ionic current pulse has subsided, by which time the conductive device has become free of residual substances. As a result, the conductive device remains uncontaminated and has a long service life. The time-averaged power consumption of the technique is less than 2 mW. For resistance heating, a meander heater element can be disposed on a silicon nitride membrane across an etched opening in a silicon chip. A separate conductive surface layer can be included in the conductive device, separated from the heater element by an insulating layer.

10 Claims, 4 Drawing Sheets

METHOD FOR DETECTING ORGANIC VAPORS AND AEROSOLS

BACKGROUND OF THE INVENTION

The invention relates to techniques for detecting organic vapors, aerosols and volatile substances, e.g., as produced in a fire.

Organic vapors and aerosols from fires can be detected by various known methods, with different methods being used in commercial smoke detectors and in laboratory equipment. Among the former are so-called ionization smoke detectors in which the air in an ionization chamber is ionized by a radioactive source, and an electric field is applied for measurement of a resulting ionic current. When an aerosol is present in the ionization chamber, the ionic current is reduced. In other commercial smoke detectors, and in measurement instruments, optical methods are used for detecting aerosols and vapors, e.g., by measuring optical transmission, spectral absorption or light scattered by aerosols. Used to a lesser extent is detection by surface ionization in which molecules are ionized thermally at a heated surface, and the ions are measured as an ionic current in an applied electric field.

In selecting a detection method, it is often desirable that different vapors and aerosols be detected with equal sensitivity. The detection of aerosols by ionization smoke detectors is reliable in this respect, as most combustion vapors and aerosols cause a reduction in the ionic current within a short time span. However, in commercial applications the need for a radioactive source to produce the ionic current causes difficulties, e.g. in the disposal of radioactive waste in the manufacture and maintenance of such detectors.

Optical detection by measuring light scattered by aerosols has different sensitivities for different combustion aerosols, as the degree of light scattering depends on the type of aerosol. Light-colored aerosols scatter incident light to a considerable degree, and more so than dark-colored aerosols.

Optical transmission measurements are superior with respect to uniformity of detection of different types of aerosols, but are difficult to carry out especially at small concentrations. The detection of small concentrations requires either a long measurement distance, or else a measurement with very high sensitivity. These measurements of transmission have been found to be difficult and of limited applicability.

Absorption measurement requires special light sources, filters and sensors which tend to be costly. Moreover, for the detection of different types of aerosols it is necessary to replace certain device components, so that this method is limited to laboratory equipment.

In the detection of vapors and aerosols by surface ionization, molecules to be detected condense at a conductive surface. To some extent, molecules are adsorbed at the surface. The molecules are ionized by heating the surface to several hundred degrees Celsius, and positive and negative ions are emitted from the surface. For measurement, emitted ions are collected by a counter-electrode which faces the surface. Depending on whether the charge of the ions to be detected is positive or negative, an opposite negative or positive potential is applied to the electrode. By measuring the resulting ionic current, ionizable molecules in the vicinity of the measurement device are detected.

Effective detection of aerosols by surface ionization depends primarily on the degree of ionizability of the molecules. The degree of ionizability depends on the temperature of the ionizing surface and on the particle ionization potential (in the case of positive ions) or the electron affinity (in the case of negative ions) as compared with the emission work function of the surface material. Positive ions are formed best when the ionization potential is low, and negative ions when the electron affinity is high.

Substances whose vapors and aerosols can be detected by surface ionization, i.e., which can be ionized at a conductive surface, include amines, hydrazines and nitrogen-containing compounds, e.g., triethylamine, trimethylamine, pentylamine, butylamine, propylamine, amino acids, acetic acids, phenols, anilines and ammonia. In particular, aerosols and vapors produced by burning pulp materials can be detected by this method.

A device for the detection of smoke particles is described in U.S. Pat. No. 4,176,311. The device has a wire of tungsten or platinum, and a cylindrical or semi-cylindrical counter-electrode. At the wire, smoke particles are ionized thermally, as wire temperature is at a constant 500° C. due to a steady electric current in the wire. There results a measurable ionic current to the counter-electrode. In commercial use especially, the limited life of the heating wire is disadvantageous. Also, as the wire becomes contaminated, the sensitivity of the device decreases over time. Moreover, for continuous heating of the wire, power consumption is relatively high.

SUMMARY OF THE INVENTION

It is an object of the invention to provide a method and a device for the detection, by surface ionization, of organic vapors and aerosols, more particularly combustion amines, hydrazines and nitrogen-containing compounds and vapors and aerosols. The inventive device avoids the disadvantages of the prior art described above: in requiring less power, in operational reliability over a longer time span, in a construction which is suitable for low-cost, automated mass production, and in ready integration with electronic components.

In a preferred detection method, ionizable molecules of organic vapors or aerosols to be detected condense and/or are adsorbed at a surface of a conductive device at room temperature, and are ionized thermally by pulsed heating of the conductive device, e.g. by resistance heating. The ionized molecules are emitted from the conductive device and collected at a collector electrode, and a resulting ionic current is amplified and measured by a signal processing circuit. After each ion emission pulse, heating of the conductive device continues until the ionic current has subsided to a stationary value corresponding to the absence of molecules. At this point, the conductive device is free of residual substances. After cooling, molecules can again condense for detection. As contamination of the conductive device is minimized, device sensitivity is sustained over a relatively long time span. Due to the pulsed heating of the conductive device, time-averaged power consumption is low. In the presence of ionizable molecules, the ionic current resulting from surface ionization has a value in the nano-ampere range, which amounts to approximately one thousand times the current measured in clean air.

The detector device includes a conductive device having an ion emission surface, and a collector electrode for collecting the emitted ions which is disposed facing the conductive device. In a preferred first embodiment, the conductive device has a resistance heater element which is disposed on a silicon nitride membrane ($Si_3N_4$) across an etched opening of a silicon chip. A preferred second embodiment further includes a conductive surface layer and As an insulating layer between the conductive surface layer and the resistance heater element.

For resistance heating, a thin-layer meander of a metal such as platinum can be used, which is heated by applying current pulses. There results a very high rate of temperature increase. In the first embodiment, ions are formed directly at the heater surface of the conductive device. Molecules adsorbed at the heater surface are ionized and emitted. In the second embodiment, ions are formed at the surface of an additional conductive layer which is heated by the resistance heater element. The ion-emitting conductive layer is separated from the resistance heater element by a thin layer of electrically insulating material. As compared with the first embodiment, this structure offers more uniform heating, across the face of an ion-emitting surface.

The conductive layer, the insulating layer, the resistance heater element, and the $Si_3N_4$ membrane can be deposited as thin layers on a standard silicon wafer, and standard chip manufacturing techniques can be used, e.g. masking and thin layer vacuum deposition. Thus, large numbers of conductive devices can be produced in automated mass production. Electronic circuitry for signal processing to measure the ionic current can be integrated on the same silicon chip, and can also be formed in automated production.

In either embodiment, pulsed heating can involve a physical effect other than resistance heating. For inductance heating, for example, a thin-film conductive inductor spiral on a suitable thin-film susceptor can be used. For optical radiation heating an infrared laser can be used.

In an electric field between the conductive device and the collector electrode, and with pulsed heating of the conductive device, ionic current pulses are produced which first rise steeply and then slowly subside. Heater power is maintained throughout a pulse, so that the conductive device go and the ion-emitting surface remain heated after the pulse has peaked. During this latter period, substances remaining at the ion-emitting surface are removed therefrom by combustion, catalytic combustion, evaporation or desorption, until the ionic current has subsided to a stationary value. When the surface is free from residual substances and the heater is turned off, the surface cools down for renewed condensation of molecules thereon. Repeated freeing from residual substances prevents the surface from becoming contaminated, and thus ensures an extended service life of the conductive device.

DETAILED DESCRIPTION OF PREFERRED EMBODIMENTS

Figure 1A:
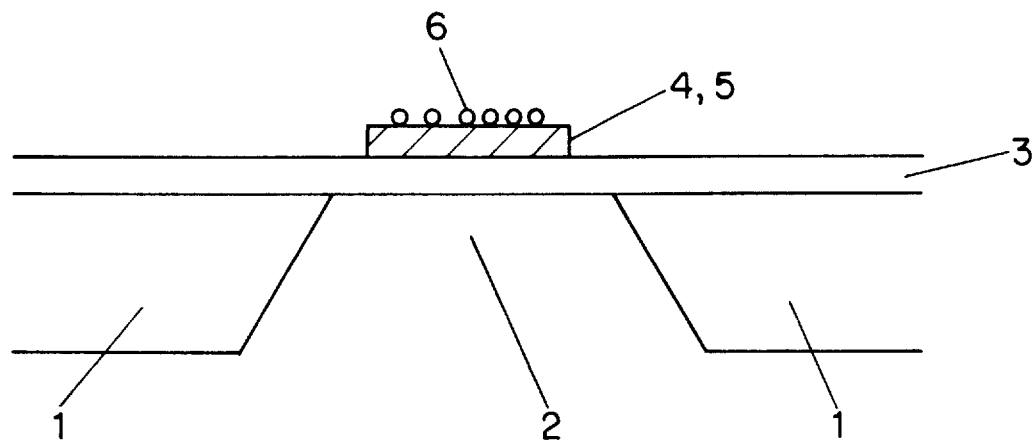
FIGS. 1a and 1b are greatly enlarged cross-sections through layered structures, respectively of the first and second preferred embodiments of the conductive device.
Figure 2:
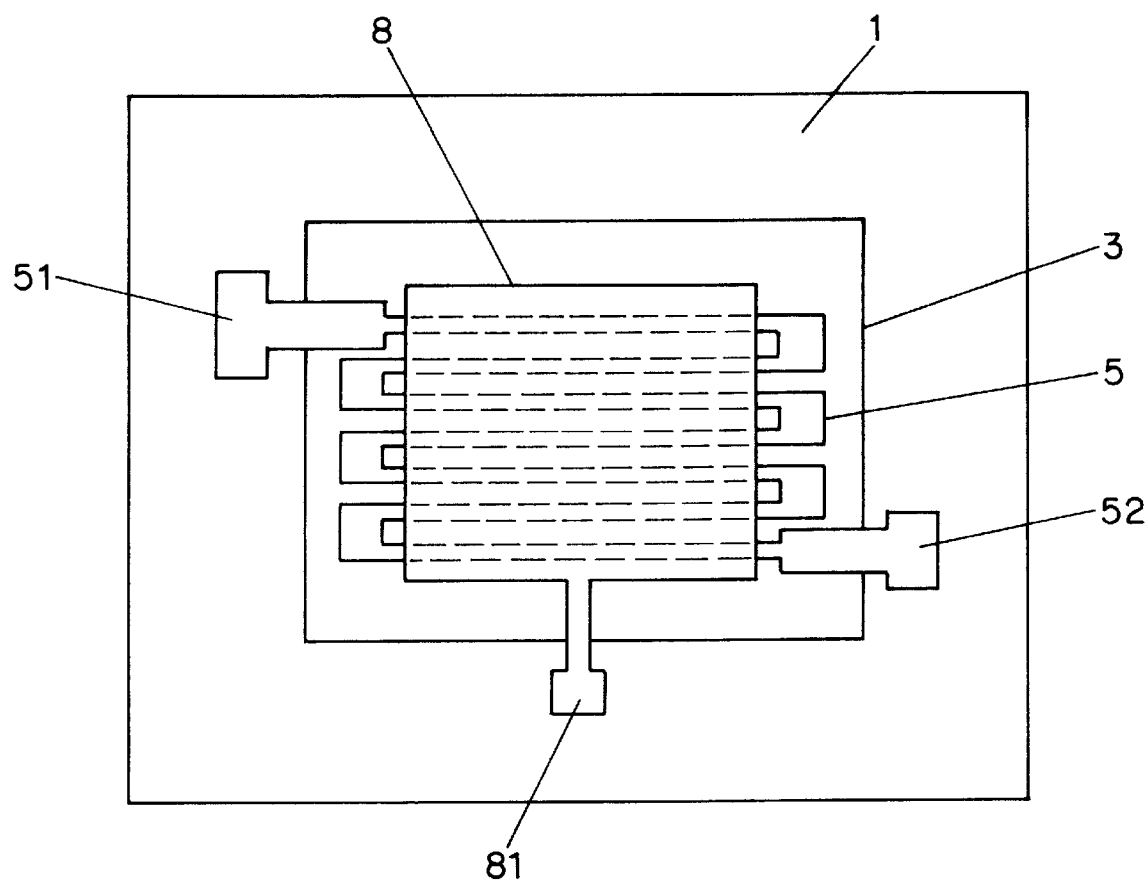
FIG. 2 is a top view of the conductive device of FIG. 1b.

FIG. 1a shows a silicon chip 1 having a central rectangular opening 2 and a deposited layer 3 of $Si_3N_4$ which extends across the opening 2. Such a structure can be made by selective etching of the opening 2 after deposition of the layer 3 on the silicon chip. Across the opening 2, the layer 3 serves as a thin membrane support layer for the conductive device 4. The thickness of the membrane 3 can be 0.6 $\mu$m, for example. The conductive device 4 is a resistive heater layer 5 which is disposed on the membrane, having a lateral extent which is slightly less than that of the opening 2. The layer 5 consists of a resistance heater material which adheres well to the $Si_3N_4$ layer 3 when deposited as a thin layer. Noble metals such as platinum are suitable for this purpose. The layer,5 forms a meander with contact terminals or pads 51 and 52 as shown in FIG. 2 for the second embodiment. Further shown are molecules 6 which are condensed and/or adsorbed at the surface of the resistive heater layer 5.

Figure 1B:
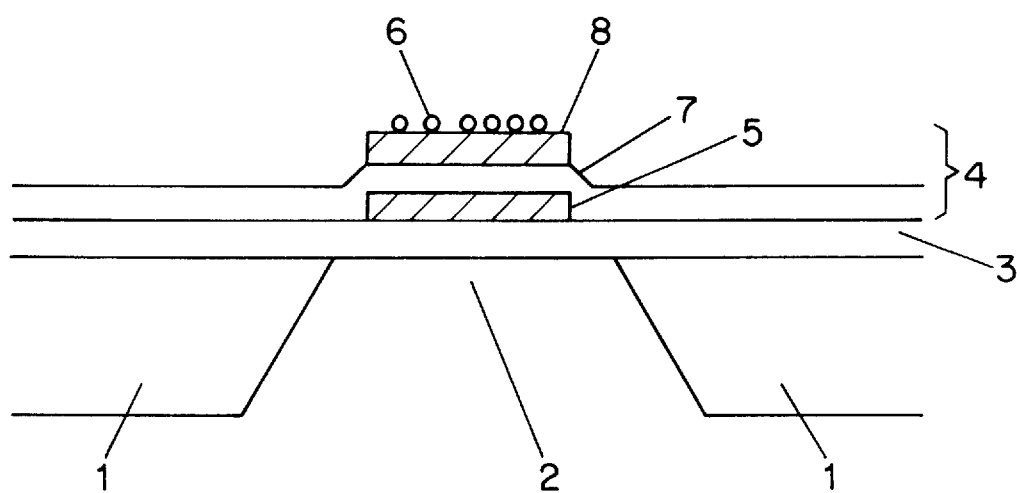

FIG. 1b shows the second embodiment of the conductive device which further includes an electrically insulating layer 7 which covers the resistive heater layer 5 across and beyond the region of the opening 2. It consists of a layer of $Si_3N_4$ for example, or a combination of superposed layers of $Si_3N_4$ and $SiO_2$. The layer 7 insulates the resistive heater layer 5 from a conductive layer 8 at whose surface ions are formed and emitted. The conductive layer 8 has essentially the same extent as the resistive heater layer 5 and consists of a sufficiently conductive material. It preferably consists of platinum, which has been found suitable for surface ionization. Alternatively, a semiconductor material can be used. The conductive layer 8, cools down between heating pulses, is shown with condensed molecules.

The silicon chip 1 has a standard thickness of 0.38 mm. The overlying layers 3, 5, 7 and 8 each have a thickness of a few 100 nanometers. Suitable layer thicknesses depend on the materials used. Intermediary layers such as suitable adhesive layers can he interposed between the layers.

FIG. 2 shows the silicon chip 1, the $Si_3N_4$, membrane 3, and the meander-shaped resistive heater 5 with electrical contact pads 51 and 52. The ion-emitting, conductive layer 8 with electrical contact pad 81 overlies the insulating layer 7 on the heater layer 5. (The layer 7, which is shown in FIG. 1b, is not shown in FIG. 2 for clarity.) The heater pattern is chosen for uniformity of heating of the conductive layer 8 across its surface. To this end, the heater has narrow, close-spaced straight conductive paths in the meander pattern. In the 180° turns of the pattern, path width is greater than in the straight segments, for lesser heating in the turns beyond the boundary of the conductive layer 8 as compared with the straight segments underlying the layer 8. Path width is about 40 $\mu$m in the straight segments and about 250 $\mu$m in the turns.

Figure 3:
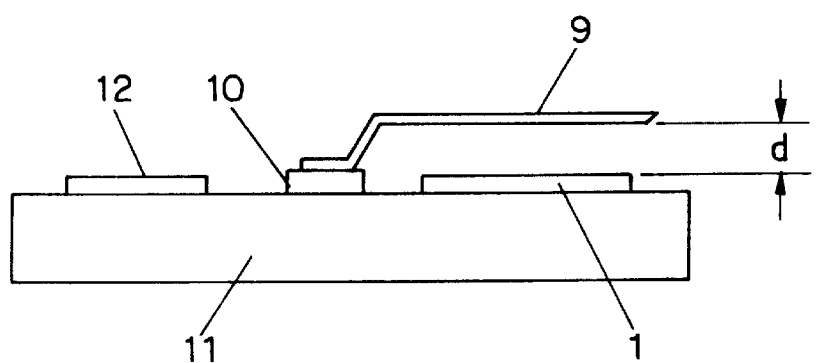
FIG. 3 is a side view of a detector device including a conductive device, an ion collector electrode, and a signal processor circuit.

FIG. 3 shows the conductive device represented by the silicon chip 1 (on which the layers 3 and 5, and, optionally, 7 and 8 are not shown). The foot of a bent collector electrode 9 is attached to an auxiliary substrate 10 which is coated with a conductive material.

For ion collection, a voltage is applied to the collector electrode via the conductive coating of the auxiliary substrate 10. The collector voltage can be chosen for a desired electric field strength, depending on the distance d between the collector electrode 9 and the conductive device on the chip 1. For example, for emission of positive ions from the surface of the conductive device, with a distance d of 0.8 mm, and with the conductive layer 8 at ground potential, the collector electrode voltage can be chosen as −100 V. As a result, in the second embodiment, a substantially uniform electrical field can be formed between the conductive layer 8 and the collector electrode 9. In the first embodiment, with the collector voltage applied, e.g., between the heater terminal 51 and the collector electrode 9, field strength will vary due to the meander pattern and the voltage drop along the pattern. A conductive device and a collector electrode can be dimensioned and disposed so that the same voltage can be used for ion collecting as for heating.

The silicon chip 1 and the auxiliary substrate 10 are disposed on a conductive, preferably gold-plated support 11, together with a signal processor circuit 12. Alternatively, instead of by discrete components, a detector device can be made as an integrated device on a single silicon chip.

Figure 4:
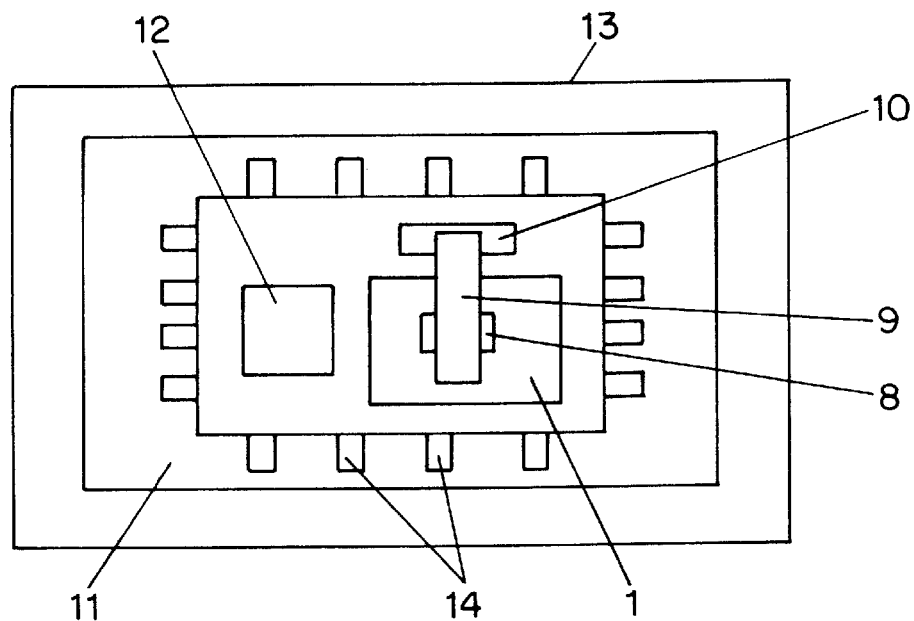
FIG. 4 is a top view of a detector device disposed in a standard integrated-chip (IC) housing.

FIG. 4 shows the detector device in a commercial IC housing 13. Electrical contact pads 14 serve to supply power to the signal processor circuit 12, the heater 5, and for supplying the collector electrode voltage. The gold-plated conductive surface 11 is disposed on the insulating material of the IC housing 13.

Figure 5:
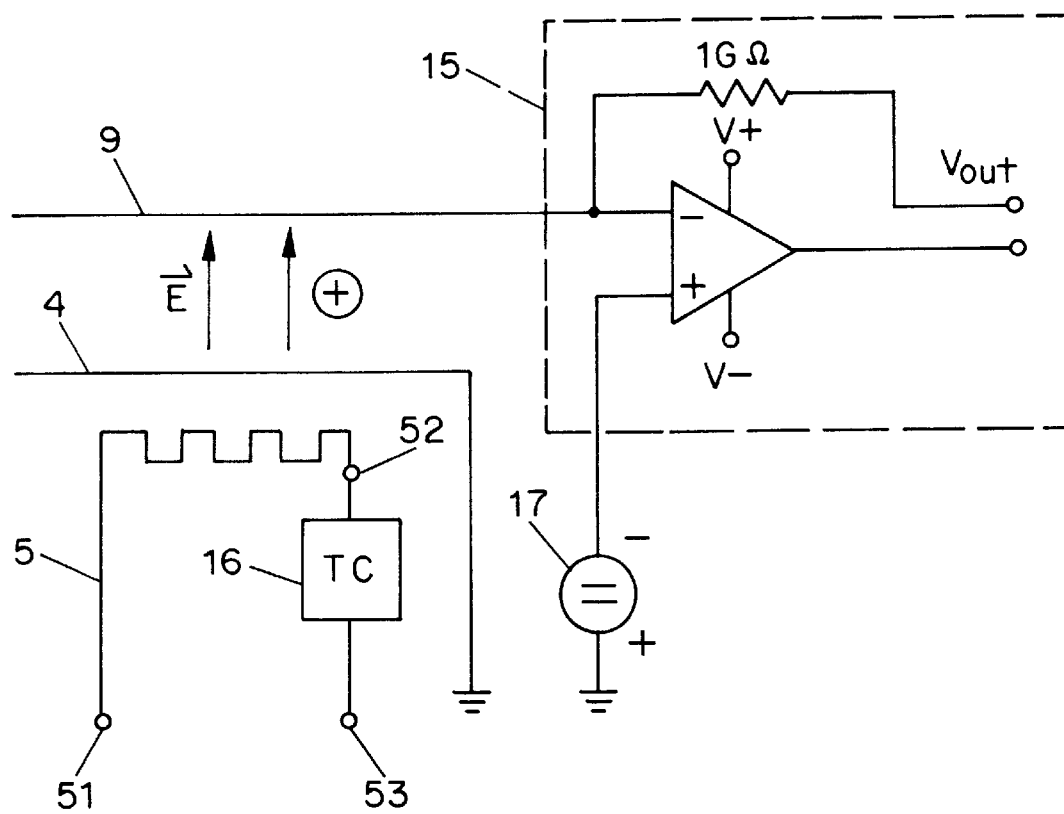
FIG. 5 is an electric circuit diagram for a preferred detector device.
Figure 6:
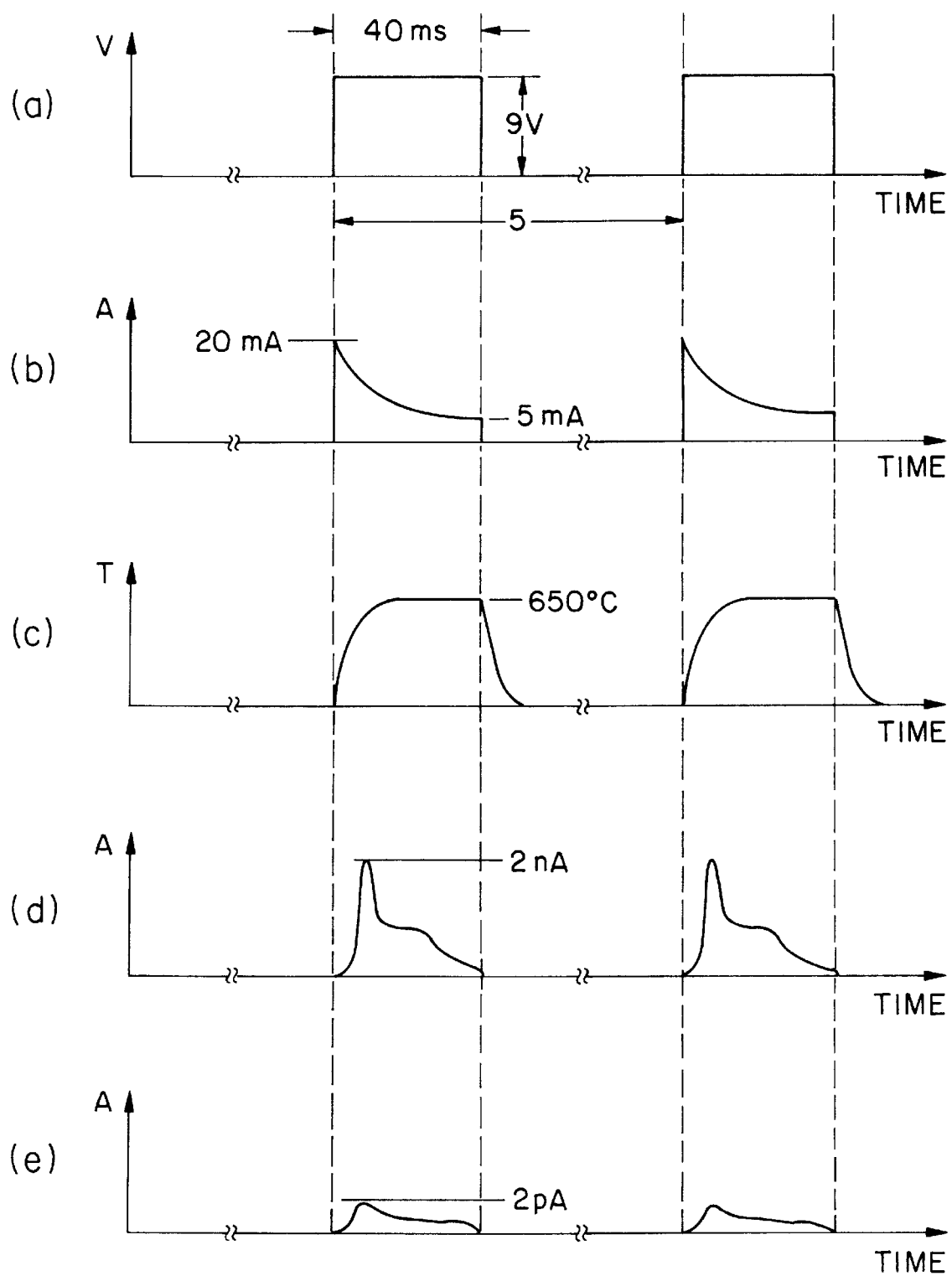
FIG. 6 includes synchronous graphs (a) through (e) of conductive device heating voltage, heating current and by temperature, and ionic current in the presence and absence of a vapor/aerosol.

FIG. 5 shows an electronic timer circuit 16 having a terminal 53, which circuit is connected to the heater terminal 52 for pulsed heating of the conductive device 4. The transimpedance circuit 15 is for detecting positive ions. The ions are collected by the collector electrode 9, and the ionic current is amplified by the circuit 15 for measurement of the voltage $V_{out}$. Typically, in the presence of ionizable, organic vapors and aerosols, the ionic current is on the order of nano-amperes. After amplification by a factor of $10^9$ V/A, measurement values are in the volt range. To suppress leakage currents, the operational amplifier of the transimpedance circuit 15 has a high input resistance, e.g. on the order of $10_{15}$ Ω. A collector bias voltage of −15 to −100 V is provided by the voltage source 17 to produce the electric field for steering the emitted ions from the conductive device 4 to the collector electrode 9.

Graph 6a shows the course of the voltage applied for resistance heating over time. The heater is operated by 9-volt pulses of 40 ms duration at 5-second intervals, for example, in which case the time-averaged power consumption is less than 2 mW. Graph 6b shows the resulting current pulse in the heater, and Graph 6c shows an estimate of the course of the heater temperature. A temperature of about 650° is reached within about 10 ms, corresponding to a temperature increase at a rate of about 60,000° C./S. After the pulse, the heater temperature subsides to room temperature within about 10 ms. Graph 6d shows an ionic current signal in the presence of aerosols, in particular of cigarette smoke. Shortly after the onset of the heater pulse, for a few milliseconds, ions are emitted from the surface of the conductive device, and the ionic current rises steeply to a peak of 2 nA and then decreases slowly. Heating continues during this period until the ionic current has subsided to a stationary value, for the surface of the conductive device to he freed from residual substances. Between heater pulses, the surface cools down and new molecules can condense. Graph 6e shows a typical ionic zero-signal current for clean air, with a peak of about 2 pA.

We claim:

1. A method for detecting an organic vapor and/or aerosol in a spatial volume between a conductive device and a collector electrode, comprising:

applying heating pulses to the conductive device and applying a voltage between the conductive device and the collector electrode, repeatedly to form ions of molecules of the organic vapor and/or aerosol and to generate ionic current pulses between the conductive device and the collector electrode, with each of the current pulses corresponding to one of the heating pulses;

detecting the current pulses; and extending each of the heating pulses for a duration until the corresponding one of the current pulses has subsided from a current peak to a stationary value, for the conductive device to be substantially freed of contaminants.

2. The method according to claim 1, wherein detecting the current pulses comprises amplifying the current pulses.

3. The method according to claim 1, wherein heating comprises resistance heating.

4. The method according to claim 1, wherein heating comprises inductance heating.

5. The method according to claim 1, wherein heating comprises optical radiation heating.

6. The method according to claim 1, wherein heating results in a temperature increase at a rate of more than 10,000° C. per second in the conductive device.

7. The method according to claim 1, wherein heating pulses are spaced at regular time intervals.

8. The method according to claim 1,wherein the heating pulse has a duration of at least 30 milliseconds.

9. The method according to claim 8, having a time-averaged heating power consumption of less than 2 mW.

10. The method according to claim 1, for detecting an organic vapor and/or aerosol selected from the group consisting of amines, hydrazines, nitrogen-containing pounds and combustion aerosols.

\* \* \* \* \*